United States Patent [19]

Nagji et al.

[11] Patent Number: 4,740,631
[45] Date of Patent: Apr. 26, 1988

[54] PROCESS FOR PREPARING ETHERS

[75] Inventors: Moez M. Nagji, Danbury, Conn.; Desh R. Garg, Hopewell Junction; William C. Miller, Katonah, both of N.Y.

[73] Assignee: Union Carbide Corporation, Danbury, Conn.

[21] Appl. No.: 679,213

[22] Filed: Dec. 7, 1984

[51] Int. Cl.$^4$ .................. C07C 41/06; C07C 41/34
[52] U.S. Cl. .................................... 568/697; 568/699
[58] Field of Search ............................. 568/697, 699

[56] References Cited

U.S. PATENT DOCUMENTS

| | | |
|---|---|---|
| 3,726,942 | 4/1973 | Louder ........................... 260/683.61 |
| 4,371,718 | 2/1983 | Hutson ................................ 568/697 |
| 4,447,653 | 5/1984 | Vora .................................... 568/697 |
| 4,490,563 | 12/1984 | Pool et al. ........................... 568/697 |
| 4,504,688 | 3/1985 | Herwig et al. ....................... 568/697 |

*Primary Examiner*—Howard T. Mars
*Attorney, Agent, or Firm*—Richard G. Miller

[57] ABSTRACT

In the process for preparing methyl tert.-alkyl ether comprising the steps of (a) contacting and reacting in the liquid phase a reaction mixture formed by combining a stream consisting essentially of $C_4$–$C_5$ hydrocarbons and containing at least some proportion of isoalkylene and a stoichiometric excess of methanol, with respect to the isoalkylene, to form a reaction product comprising methyl tert.-alkyl ether, unreacted methanol and unreacted $C_4$–$C_5$ hydrocarbons; (b) isolating the methyl tert.-alkyl ether from the reaction product; and (c) recovering the unreacted methanol from the residual portion of the reaction product; the improvement which comprises selectively adsorbing the methanol constituent of said residual reaction product in a bed of crystalline molecular sieve adsorbent and recovering same by desorption using as a purge-desorption stream, the $C_4$–$C_5$ hydrocarbon stream used to prepare the initial reaction mixture.

4 Claims, 1 Drawing Sheet

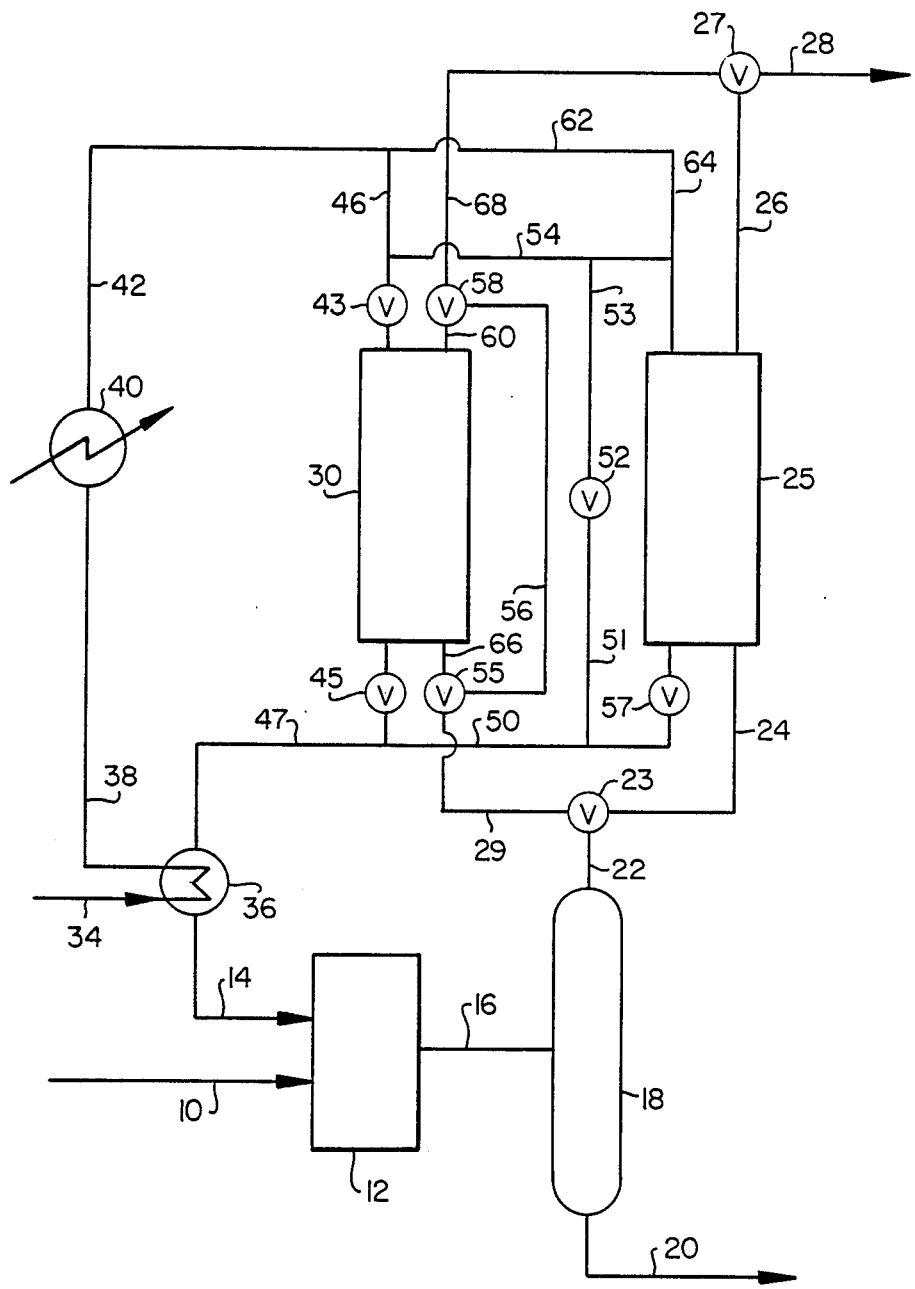

PROCESS FOR PREPARING ETHERS

The present invention relates in general to the preparation of ethers by the reaction of an alcohol with an isoolefin. More particularly, it relates to the preparation of methyl tertiary alkyl ether by the reaction of a tertiary isoolefin containing four or five carbon atoms with a stoichiometric excess of methanol wherein the unreacted methanol in the reaction product is recovered by adsorption in a molecular sieve bed followed by desorption therefrom using as the purge-desorption medium, the hydrocarbon feedstock which is subsequently to be reacted with methanol to produce additional methyl tert.-alkyl ether.

BACKGROUND OF THE INVENTION

The production of ethers by the reaction of an isoolefin and an alcohol is a well-known commercial operation. A number of detailed descriptions of such processes, particularly as they relate to the production of methyl tert.-butyl ether, are contained or referenced in recently issued U.S. Pat. No. 4,447,653 (B.V. Vora) and in the Hanes et al. U.S. Pat. No. 4,418,219 issued Nov. 29, 1983, both of which are incorporated by reference herein. Such procedures are, in general, also applicable to the production of methyl tert.-amyl ether.

Both methyl tert.-butyl either (MBTE) and methyl tert.-alkyl ether (MTAE) are useful as high octane blending agents for gasoline motor fuels by virtue of their high Research Octane Number (RON) of about 120. Perhaps the most commonly employed reaction in the preparation of MTBE and MTAE is that between methanol and isobutylene or isoamylene, respectively. A wide variety of catalyst materials have been found to promote this reaction including ion-exchange resins such as a divinylbenzene cross-linked polystyrene ion exchange resin in which the active sites are sulfuric acid groups: and inorganic heterogeneous catalysts such as boric acid, bismuth molybdate, and metal salts of phosphomolybdic acids wherein the metal is lead, antimony, tin, iron, cerium, nickel, cobalt or thorium. Also boron phosphate, blue tungsten oxide and crystalline aluminosilicates of the zeolitic molecular sieve type have also been proposed as heterogeneous catalysts for the reaction of methanol and isobutylene.

The preference for the isoalkylene-methanol reaction is in part, at least, due to the relative abundance of the starting materials. Both isobutylene and isoamylene are readily available in a petroleum refinery from both fluid catalytic crackers and as a by-product of ethylene production. Methanol is, of course, a staple commercial chemical of long standing. Moreover, isobutylene, because of its volatility, cannot be added to the gasoline pool without alkylation. Methanol cannot be added to gasoline in significant quantities because of immiscibility problems and because of its corrosiveness toward existing internal combustion engines. The combining of these two compounds thus appears to be an advantageous way to extend the gasoline pool. The modification of a gasoline by the conversion of 2-methyl-1-butene and 2-methyl-2-butene to methyl tert.-amyl ether is proposed in U.S. Pat. No. 3,482,952.

In addition to being useful in the preparation of high octane ethers for gasoline up-grading, the etherification process is also useful as a separation process. The reaction of methanol with mixed $C_4$ and $C_5$ olefins is selective for isobutylene and isoamylene. Therefore, a mixed butylene and/or amylene stream common to refineries can use the aforesaid etherification process to separate this mixture and to produce a stream of essentially pure normal butenes and/or amylenes and essentially pure MTBE and/or MTAE. The ethers can subsequently be cracked to produce essentially pure isoalkylenes.

A wide variety of reaction conditions have heretofore been proposed for carrying out the reaction of isobutylene or isoamylene with methanol, depending in part upon the type of catalyst employed in each case. Thus, both vapor phase and liquid phase processes are known in which reaction temperatures are from about 50° C. to about 400° C., pressures vary from atmosphere to 1,500 psig, and the mole ratios of methanol to isoalkylene range from 0.1:1.0 to about 10:1. Both batch type and continuous process schemes are said to be suitably employed.

It is commonly the case that the source of isobutylene is a mixed $C_4$ hydrocarbon stream from a refinery operation, and the reaction with methanol is carried out in the liquid phase at a temperature not exceeding 100° C. The quantity of the MTBE produced depends upon the isobutylene content of the $C_4$ hydrocarbon stream used. When a $C_4$ hydrocarbon stream cut from steam cracking is used, providing a feedstock with approximately 50% isobutylene after butadiene extraction, the reactor effluent can contain almost 60% MTBE and can sometimes be used as a gasoline component without further treating. It is generally more desirable, however, to separate the unreacted $C_4$s from the reactor effluent by distilling off the unconverted $C_4$s. When this is done, MTBE of about 98% purity can be produced at an isobutylene conversion of approximately 95%. A further increase in conversion can be achieved only by using a higher methanol/isobutylene ratio in the reactor feedstock. Because greater than stoichiometric amounts of methanol are used in the high conversion MTBE processes (also to allow for fluctuating isobutylene concentrations), additional steps have to be included in such processes to recover the excess methanol from reactor effluent. The recovered methanol is then recycled to the reactor feed stream.

When the source of isobutylene is a mixed $C_4$ hydrocarbon stream from a fluidized catalytic cracking (FCC) process, the isobutylene usually constitutes only about 12 to 16% of the total $C_4$'s. With such feedstocks, the economics of the etherification process favors the use of a substantial excess of methanol, thereby increasing the importance of effective recovery and recycle of unreacted methanol.

In the prior known high conversion MTBE processes, the excess methanol is usually recovered by a combination of distillation and water washing steps. The reactor effluent containing MTBE, unconverted methanol and $C_4$ hydrocarbons is fed to a debutanizer tower wherein the unreacted $C_4$'s are distilled off as the overhead stream together with some methanol. The methanol from this stream is recovered by a water wash step and subsequent distillation of the resulting water-methanol solution. The mixed $C_4$ hydrocarbons are routed to an appropriate processing point in the refinery such as an alkylation unit. The recovered methanol is recycled back to reactor feed. The bottoms from the debutanizer tower contain MTBE and methanol. This stream can, if desired, be distilled in a tower to recover MTBE product as the bottoms. The methanol-MTBE azeotrope (approximately 10 wt. % MEOH) is recovered overhead and recycled back to reactor feed thereby completing methanol recovery.

It will be understood by those skilled in the art that the foregoing observations concerning the commercial sources of isobutylene and the general procedures for converting this $C_4$ isoalkylene to MTBE apply with equal validity to isoamylene and its conversion to MTAE provided the corresponding $C_5$ hydrocarbons are substituted for the $C_4$ hydrocarbons. For this reason, it will also be understood that whereas the processes of the present invention are hereinafter illustrated with reference to $C_4$ hydrocarbons and MTBE, the illustrations also serve to describe the processes in which $C_5$ hydrocarbons are utilized in the ultimate production of MTAE. Also mixed $C_4$ and $C_5$ hydrocarbon streams, feedstock and the like can also be substituted for their pure $C_4$ and $C_5$ counterparts.

STATEMENT OF THE INVENTION

It has now been discovered that the unreacted methanol in the reaction product of a high conversion MTBE or MTAE process can be recovered in a highly effective and efficient manner and recycled to the reactor with additional isobutylene and/or isoamylene without the need for water-washing and the necessary and energy-intensive distillation of the resultant aqueous methanol solution. In accordance with the present improved process the residue of the reaction product after removal of the methyl tert.-alkyl ether which comprises principally methanol and unreacted $C_4$'s and/or $C_5$'s along with relatively small amounts of oxygenated hydrocarbon by-products, particularly dimethyl ether, can be passed into an adsorption bed of an appropriate molecular sieve adsorbent wherein the methanol is selectively adsorbed and the unadsorbed $C_4$'s and/or $C_5$'s and dimethyl ether recovered as the effluent from such bed and further treated, if desired, to remove the dimethyl ether. The adsorbed methanol is removed from the bed periodically by purge desorption using as the purge the same mixed $C_4$ and/or $C_5$ hydrocarbon stream which ultimately is, in combination with the desorbed methanol, fed to the reactor to produce additional MTBE and/or MTAE, and the cycle repeated.

As a further improvement, the process of the present invention provides for the removal of the by-product dimethyl ether (DME) from the unreacted $C_4$'s and/or $C_5$'s by selectively adsorbing the DME in another molecular sieve bed containing an adsorbent particularly suited for such purpose. This is essential if these unreacted hydrocarbons are to be utilized as a part of the feedstock in an alkylation process catalyzed by HF, since DME is a catalyst poison in such systems.

In summary, in the process for preparing methyl tert.-alkyl ether which comprises the steps of (a) contacting and reacting in the liquid phase a reaction mixture formed by combining a stream consisting essentially of hydrocarbons having from 4 to 5 carbon atoms and containing at least some proportion of an isoalkylene having from 4 to 5 carbon atoms with a stoichiometric excess of methanol, with respect to the isoalkylene, to form a reaction product comprising methyl tert.-alkyl ether, unreacted methanol and unreacted $C_4$–$C_5$ hydrocarbons and optionally dimethyl ether;

(b) isolating the methyl tert.-alkyl ether from the reaction product: and (c) recovering the unreacted methanol from the residual portion of the reaction product; an improvement in the recovery of unreacted methanol from the reaction product can be achieved by utilizing the following procedure:

(d) separating the unreacted methanol from the residual portion of the reaction product by passing said residual portion in the liquid phase and at a temperature of less than 120° C. through an adsorbent bed containing a molecular sieve adsorbent capable of selectively adsorbint methanol, wherein methanol is adsorbed and non-adsorbed $C_4$–$C_5$ hydrocarbons are removed as an effluent therefrom;

(e) recovering the adsorbed methanol from said adsorption bed by purge-desorption wherein a purge stream in the liquid phase and at a temperature of from about 50° C. up to about 121° C. is passed through said bed, said purge stream being an additional portion of $C_4$–$C_5$ hydrocarbon stream of the aforesaid process step (a); and (f) passing the liquid effluent from the adsorption bed in step (e) to a reactor as feedstock thereto for the formation of additional methyl tert-alkyl ether.

IN THE DRAWINGS

The sole FIGURE of the drawings is a schematic flow diagram illustrating one embodiment of the present invention.

DETAILED DESCRIPTION OF THE INVENTION

The following description of the present process with respect to the production of MTBE is made with reference to the flow diagram of the drawings. In the interest of simplifying the description of the invention, the process system in the drawing does not contain the several conduits, valves and the like which in actual practice would be provided to enable the process to be carried out continuously. Such details of construction are well known to those of routine skill in the art.

Methanol in the liquid phase enters the reaction system through line 10 and enters the reactor 12 along with a $C_4$ hydrocarbon liquid stream comprising isobutylene and containing additional methanol entering through line 14. Advantageously all fluid streams introduced into the system have previously been dried to a water dew point of 0° to 10° C. at the operating pressure of the reactor. Reactor 12 is operated at a temperature which in large measure is dependent upon the particular catalyst employed but is generally in the range of about 65° C. to 90° C. and using an internal system pressure sufficient to maintain the reaction mixture in the liquid phase. In the present embodiment, the catalyst is of the ion-exchange resin type and the temperature of the reactor is about 90° C. The isobutylene-containing $C_4$ feedstock comprises a mixture of one or more other $C_4$ hydrocarbons including butene-1, cis and trans butene-2, butadiene, isobutane and n-butane along with the isobutylene. Preferably the isobutylene is present in an amount of at least 10 mol-%. The molar ratio of methanol to isobutylene is greater than 1.0 and is preferably between 2:1 to 10:1. The effluent from the reactor comprises product MTBE, unreacted methanol, unreacted $C_4$'s and small to trace amounts of dimethylether and other reaction by-products. This effluent is passed through line 16 to distillation unit 18. While in this illustration the reactor and distillation tower are represented as two separate apparatuses, relatively recent advances have made possible the combination of the function of the reactor and the distillation tower into a single piece of apparatus. For purposes of the present invention, either operational mode is suitably employed. As a result of the distillation process, MTBE product is recovered from the bottom and is removed from the system through line 20. The overhead effluent from the distillation tower comprises from about 0.5 to 4.0 volume percent unreacted methanol, unreacted $C_4$ hydrocarbons, 200 to 400 ppm(v.) dimethylether and other volatile by-products. This effluent passes through line 22, valve 23 and line 25 to adsorbent bed 25 containing a molecular sieve adsorbent in a partially activated state, i.e., having capacity to adsorb methanol. The particular molecular sieve used as the adsorbent is not a critical factor provided that it has pores large enough to adsorb methanol. The most readily available on a commercial basis are the well-known crystalline aluminosilicate (zeolite) molecular sieves such as zeolite A, zeolite X and zeolite Y, but more recently developed non-zeolitic molecular sieves are also suitably employed, such as the crystalline microporous aluminophosphates disclosed in U.S. Pat. No. 4,310,440 and the silicoaluminophospates disclosed in U.S. Pat. No. 4,440,871. The preferred adsorbent for this purpose is the sodium cation form of zeolite A having pore diameters of about 4 Angstroms (zeolite 4A). Zeolite A is described in detail in U.S. Pat. No. 2,882,243. Although zeolite 4A has a significant adsorptive affinity for butadiene, it exhibits only a relatively small capacity for singly unsaturated and paraffinic $C_4$'s, and thus preferentially adsorbs methanol from admixture with the $C_4$ hydrocarbons. The temperature within adsorption bed is preferably at an initial temperature of from 30° C. to 120° C. The actual bed temperature will depend upon the temperature of the purge gas used to desorb the bed during the previous bed regeneration, and whether or not a bed cool-down step was employed just prior to the commencement of the adsorption step wherein effluent from distillation unit 18 is treated to remove methanol therefrom. In a preferred embodiment, the temperature of bed 25 at the beginning of the adsorption step is from about 75° C. to about 120° C. as a result of using a hot purge desorption procedure without a subsequent bed cooldown as described in greater detail hereinafter. The effluent from the distillation unit 18 is at a temperature of from about 30° C. to 80° C. and enters bed 25 at the same temperature. Thus at the beginning of the adsorption step, bed 25, the incoming fluid stream is at a lower temperature than the adsorbent in bed 25. As the adsorption step continues, the bed is cooled appreciably by the passage of the fluid stream. The pressure in bed 25 is maintained such as to cause the methanol-$C_4$ fluid stream being treated therein to be in the liquid phase. The effluent from bed 25 contains from about 500 to 1000 ppm(v.) methanol and about 200–2000 ppm(v.) dimethyl ether, with the balance being principally a mixture of olefinic and saturated n-$C_4$ hydrocarbons. This effluent is passed through line 26, valve 27 and line 28 and can be removed from the process system without further treatment. If, however, it is desirable to remove the d-methyl ether, or other oxygenated hydrocarbon by-product species, the effluent from bed 24 is further treated in an auxiliary bed which contains a molecular sieve adsorbent of appropriate pore size to selectively adsorb such oxygen-containing molecules. While the adsorption step is being carried out in bed 25, bed 30 is being regenerated after previous service in methanol removal from the same feedstock. The regeneration of bed 30 is accomplished by purging, preferably in a direction countercurrent to the direction of flow through the bed during the adsorption step therein, using the same $C_4$ hydrocarbon feedstock which, in conjunction with methanol, is fed to reactor 12. This $C_4$ hydrocarbon feedstock enters the system through line 34 and passes through heat-exchanger 36, line 38 and heater 40 wherein its temperature is raised to the range of at least 50° C. (122° F.), preferably at least about 80° C. (176° F.) up to about 121° C. (250° F.). Preferably the temperature of the purge stream is from about 80° C. to about 115° C. The pressure conditions are controlled to maintain the $C_4$ hydrocarbon stream through bed 30 substantially in the liquid phase. From heater 40 the hydrocarbon stream is passed through lines 42 and 46 and valve 43 into adsorbent bed 30. The effluent desorbed methanol and $C_4$ purge stream from bed 30 are, depending upon the temperature of the entering purge stream, either passed in its entirety through valve 45 and line 47 to heat exchanger 36, or some portion thereof is recycled to the ingress end of bed 30 through lines 50 and 51, valve 52, lines 53 and 54 and valve 43. If the temperature of the purge stream entering bed 30 from heater 40 through line 42 and valve 43 is at a temperature greater than about 115° C., the volume of purge fluid will, in normal practice, be sufficient to regenerate bed 30 to the required degree using a single pass through the bed. At lower temperatures, however, recycle of a portion of the purge will be required—the proportion being dependent upon the existing temperature of the purge stream. In order to effectively regenerate bed 30 using the partial recycle mode of operation, it is advantageous to terminate the recycle flow before regeneration is complete and finish the regeneration using a recycle-free purge stream from line 42. Optionally, the recycled bed effluent can be reheated prior to being admixed with fresh purge from line 42. Regardless of the regeneration mode employed, the effluent from bed 30 eventually is all passed via line 47 through heat exchanger 36 wherein its temperature is decreased to about 60° C. to 95° C., i.e., a temperature suitable for operation of the reactor 12, to which it is passed via line 14. The purge-regeneration of bed 30 is continued until desired level of residual methanol loading is achieved. At this point adsorption bed 25 is at the end of the adsorption stage in its operation and is ready to be regenerated as described above with respect to bed 30. Also at this point, the void space in bed 30 contains essentially the same hydrocarbon feedstock as enters the system through line 34, and the void space of bed 25 contains essentially the same hydrocarbon-methanol mixture which is the raffinate from distillation unit 18. In order to reduce contamination of the feedstock to reactor 12 with the void space bed volume of n-$C_4$'s from bed 25, and also to minimize the contamination of the n-$C_4$ stream leaving bed 25 through line 26 with the void space volume of isobutylenecontaining $C_4$'s of bed 30, it is a preferred embodiment of the present invention to change beds 30 and 25 from a regeneration mode to an adsorption mode, and vice versa, respectively using the following procedure: At the end of the regeneration stage in bed 30, the purge stream passing through lines 42 and 46 and valve 43 is diverted through line 54, line 53, valve 52, line 51 and valve 57 to the ingress end of bed 25. Simultaneously, the stream passing through line 22, valve 23 and line 24 is diverted through line 29, valve 55, line 56, valve 58 and line 60 to the ingress end of bed 30. The flow of these two diverted streams is continued, without any change being made in the exit flow path from either of beds 25 or 30, just until the residual void space bed volume of each bed is replaced by the newly entering stream in each case. In order to avoid contaminating the n-C$_4$ hydrocarbon stream leaving the system through line 28 with methanol contained in the void space of bed 25, it is advantageous to terminate the adsorption step in that bed at a point when the bed still contains sufficient capacity to adsorb the methanol content of the void space feedstock. At the point when the residual void space bed volume of both beds 25 and 30 have been replaced, the flow paths of the streams leaving the beds is changed so that each of the beds returns to its normal adsorption and regeneration mode as described hereinbefore. Thus regeneration of bed 25 is accomplished by directing the flow of the purge stream from line 42 through lines 62 and 64 into bed 25 and recovering the purge stream and desorbed methanol through valve 57 lines 50 and 47, heat exchanger 36 and line 14 into reactor 12. In bed 30, an adsorption stage is begun by directing the flow of the stream from distillation unit 18 through line 22, valve 23, line 29, valve 55 and line 66, and recovering the n-C$_4$ content thereof through line 60, valve 58, line 68, valve 27 and line 28.

In the foregoing embodiment of the present process, the procedure does not necessitate a period of cool-down of the adsorption beds 30 and 25 after regeneration and before each is again switched to an adsorption mode to treat the overhead feed from distillation tower 18. This omission of a cool-down period maximizes the amount of methanol desorbed from the bed and improves the delta loading of methanol thereon despite the fact that the capacity of the hot adsorbent for adsorbing incoming methanol is lower then if an adsorbent cooling stage had been employed. It is found that the feasibility of this non-cooling type of operation is due in part to the fact that the cooling front through the bed on adsorption is about five times faster than the methanol adsorption front so that the adsorption stage feedstock serves also as a bed cool-down stream. It is possible that during the initial stages of the adsorption step, the bed temperature will be too high to permit the degree of methanol removal desired, i.e., there may be leakage of small amounts of methanol in the effluent from bed 24. In such cases, the bed effluent can be passed through an auxiliary bed or to complete the methanol removal. As an alternative procedure, methanol leakage from adsorbent bed 24 or 32 during the initial stages of the adsorption step can be prevented by starting such step with the bed at a temperature below about 50° C. This can be accomplished by cooling the bed after the previous hot purge regeneration. By way of illustration using bed 25 of the drawing, this comprises continuing the flow of the C$_4$ hydrocarbon purge stream through bed 25 after regeneration but avoiding the heating in heater 40. A further decrease in the temperature of this purge gas can be accomplished in the known manner using conventional cooling means. The aforesaid process avoids many of the major problems encountered if an attempt is made to utilize a conventional thermal swing type of adsorption cycle using an extraneous inert purge gas, i.e., one that is not utilized in the process for any purpose other than purge desorption (such as nitrogen or methane) in order to recover the unreacted methanol. For instance, methanol readily forms adsorbent-deactivating coke on many zeolitic molecular sieves at high regeneration temperatures, and even if satisfactorily desorbed from the zeolite using nitrogen or methane, for example, it is difficult to condense the methanol from such a gas mixture. Also suitable inert gas streams are not always available in refineries which are most often ready sources of isobutylene. By using liquid phase and adsorption and regeneration, low temperatures can be employed which minimize coke formation on the adsorbent mass.

EXAMPLE 1

The effectiveness of the methanol adsorption and recovery aspects of the present invention were established using bench-scale adsorption apparatus and using a simulated reactor effluent characteristic of those well-known in the art. Approximately twentyfive grams of Linde type 4A molecular sieve adsorbent, 16×40 mesh particles, was packed in a fixed bed adsorption column constructed from one-half inch schedule 40 stainless steel pipe. The adsorbent was vacuum activated overnight at about 550° F. prior to use in this test. The C$_4$ hydrocarbon feed stream to the adsorption column comprised of 49.2 weight percent each of isobutane and isobutylene and contained 1.6 weight percent methanol. The regeneration liquid feed contained 50 weight percent each of isobutane and isobutylene. The C$_4$ hydrocarbon feed containing 1.6 weight percent methanol was passed through the adsorption column at a flow rate of 5.5 cc/min at 75° F. and 300 psig pressure. The effluent from the adsorption column was analyzed via gas chromatology and monitored for methanol content. In order to determine the equilibrium methanol loading on the adsorbent, the adsorption process was continued until the methanol concentration in the effluent from the adsorption column became equal to the methanol concentration in the C$_4$ hydrocarbon feed to the adsorption column. A methanol mass balance was performed at the end of the experiment and established that the vacuum activated 4A molecular sieve adsorbent used had a first cycle methanol capacity of 17.2 weight percent. This indicated that this molecular sieve does suitably adsorb significant amount of methanol from a mixed C$_4$ hydrocarbon stream. The adsorbent contained in the adsorption column was then regenerated in liquid phase using a methanol-free 50-50 isobutane-isobutylene (wt. %) stream at 250° F. and 500 psig at a flow rate of 4.5 cc/minute. The regeneration process was continued until the amount of regeneration liquid used was about 55 cc/gram of adsorbent. The adsorption process was resumed at conditions identical to those used earlier in order to determine the delta loading for methanol following liquid phase adsorption. The second cycle methanol loading was measured to be 7.8 weight percent which is adequate for an efficient process.

EXAMPLE 2

In order to determine that the process is feasible with vastly different makeup of C$_4$ hydrocarbons present in the feedstock, another test was made using for adsorption a simulated feed stream containing 1.8 weight percent methanol and 90.2 weight percent isobutane and no isobutylene. Regeneration of the methanol loaded adsorbent was accomplished using 100% isobutane stream. The adsorbent used was 4A molecular sieve, 16×40 mesh. Both adsorption and regeneration were carried out in the manner described in Example 1. Adsorption was carried out at 75° F. and 300 psig while regeneration step was done at 250° F. and 500 psig. The amount of regeneration liquid used was about 40 cc/gram of adsorbent. The first cycle, vacuum activated adsorbent methanol loading was determined to be 19.1 weight percent. The methanol delta loading following liquid phase regeneration was determined to be greater than 5 weight percent.

What is claimed is:

1. In the process for preparing methyl tert.-alkyl ether which comprises the steps of
   (a) contacting and reacting in the liquid phase a reaction mixture formed by combining a stream consisting essentially of hydrocarbons having from 4 to 5 carbon atoms and containing at least some proportion of an isoalkylene having from 4 to 5 carbon atoms with a stoichiometric excess of methanol, with respect to the isoalkylene, to form a reaction product comprising methyl tert.-alkyl ether, unreacted methanol and unreacted $C_4$–$C_5$ hydrocarbons and optionally dimethyl ether;
   (b) isolating the methyl tert.-alkyl ether from the reaction product; and
   (c) recovering the unreacted methanol-containing residual portion of the reaction product;
   (d) separating the unreacted methanol from the residual portion of the reaction product by passing said residual portion in the liquid phase and at a temperature of less than 120° C. through an adsorption bed containing a molecular sieve adsorbent capable of selectively adsorbing methanol, wherein methanol is adsorbed and non-adsorbed $C_4$–$C_5$ hydrocarbons are removed as an effluent therefrom;
   (e) recovering the adsorbed methanol from said adsorption bed by purge-desorption wherein a purge stream in the liquid phase and at a temperature of from about 50° C. up to about 121° C., is passed through said bed, said purge stream being an additional portion of $C_4$–$C_5$ hydrocarbon stream of the aforesaid process step (a); and
   (f) passing the liquid effluent from the adsorption bed in step (e) to a reactor as feedstock thereto for the formation of additional methyl tert.-alkyl ether; the improvement which comprises passing the liquid effluent from step (e) through an auxiliary adsorption bed to decrease, by selective adsorption, any dimethyl ether content thereof and passing the dimethyl ether depleted effluent to a reactor as feedstock in accordance with step (f).

2. Process according to claim 1 wherein the product methyl tert.-alkyl ether is methyl tert.-butyl ether and the reaction mixture of step (a) consists essentially of methanol and $C_4$ hydrocarbons containing at least some proportion of isobutylene.

3. In the process for preparing methyl tert.-butyl ether which comprises the steps of
   (a) contacting and reacting in the liquid phase a reaction mixture formed by combining a stream consisting essentially of hydrocarbons having 4 carbon atoms and containing at least some proportion of an isobutylene with a stoichiometric excess of methanol, with respect to the isobutylene, to form a reaction product comprising methyl tert.-butyl ether, unreacted methanol and unreacted $C_4$ hydrocarbons and optionally dimethyl ether;
   (b) isolating the methyl tert.-butyl ether from the reaction product; and
   (c) recovering the unreacted methanol-containing residual portion of the reaction product;
   (d) separating the unreacted methanol from the residual portion of the reaction product by passing said residual portion in the liquid phase and at a temperature of less than 120° C. through an adsorption bed containing a molecular sieve adsorbent capable of selectively adsorbing methanol, wherein methanol is adsorbed and non-adsorbed $C_4$ hydrocarbons are removed as an effluent therefrom;
   (e) recovering the adsorbed methanol from said adsorption bed by purge-desorption wherein a purge stream in the liquid phase and at a temperature of from about 50° C. up to about 121° C., is passed through said bed, said purge stream being an additional pattern of the $C_4$ hydrocarbon stream of the aforesaid process step (a); and
   (f) passing the liquid effluent from the adsorption bed in step (e) to a reactor as feedstock thereto for the formation of additional methyl tert.-butyl ether; the improvement which comprises following the termination of the purge-desorption in step (e), the adsorption bed is utilized in the procedure of step (d) without intervening substantial cooling thereof.

4. In the process for preparing methyl tert.-alkyl ether which comprises the steps of
   (a) contacting and reacting in the liquid phase a reaction mixture formed by combining a stream consisting essentially of hydrocarbons having from 4 to 5 carbon atoms and containing at least some proportion of an isoalkylene having from 4 to 5 carbon atoms with a stoichiometric excess of methanol, with respect to the isoalkylene, to form a reaction product comprising methyl tert.-alkyl ether, unreacted methanol and unreacted $C_4$–$C_5$ hydrocarbons and optionally dimethyl ether;
   (b) isolating the methyl tert.-alkyl ether from the reaction product;
   (c) recovering the unreacted methanol-containing residual portion of the reaction product;
   (d) separating the unreacted methanol from the residual portion of the reaction product by passing said residual portion in the liquid phase and at a temperature of less than 120° C. through an adsorption bed containing a molecular sieve adsorbent capable of selectively adsorbing methanol, wherein methanol is adsorbed and non-adsorbed $C_4$–$C_5$ hydrocarbons are removed as an effluent therefrom;
   (e) recovering the adsorbed methanol from said adsorption bed by purge-desorption wherein a purge stream in the liquid phase and at a temperature of from about 50° C. up to about 121° C., is passed through said bed, said purge stream being an additional portion of $C_4$–$C_5$ hydrocarbon stream of the aforesaid process step (a); and
   (f) passing the liquid effluent from the adsorption bed in step (e) to a reactor as feedstock thereto for the formation of additional methyl tert.-alkyl ether; the improvement which comprises cyclically carrying out steps (d) and (e) in each molecular sieve-containing adsorption bed, and intermediate the change from one of the said steps to the other, the fluid held in the bed void space is replaced by an equivalent amount of the fluid of the stream to be passed through the bed in the immediate next step of the cycle, said replacement of void space fluids being carried out in a direction cocurrent with the direction of the stream passing through said bed immediately prior to the fluid replacement, and the replaced fluid being isolated from the bed effluent produced during the next immediate cyclic step in said bed.

* * * * *